US007356118B2

(12) United States Patent  
Might et al.

(10) Patent No.: US 7,356,118 B2  
(45) Date of Patent: Apr. 8, 2008

(54) ANGLED-BEAM DETECTION SYSTEM FOR CONTAINER INSPECTION

(75) Inventors: Matthew B. Might, Atlanta, GA (US); Mark A. Ferderer, Buford, GA (US); Gary F. Bowser, Auburn, IN (US)

(73) Assignee: ScanTech Holdings, LLC, Atlanta, GA (US)

( * ) Notice: Subject to any disclaimer, the term of this patent is extended or adjusted under 35 U.S.C. 154(b) by 0 days.

(21) Appl. No.: 11/258,832

(22) Filed: Oct. 24, 2005  
(Under 37 CFR 1.47)

(65) Prior Publication Data

US 2006/0233302 A1  Oct. 19, 2006

Related U.S. Application Data

(60) Provisional application No. 60/621,261, filed on Oct. 22, 2004.

(51) Int. Cl.  
*G01N 23/04* (2006.01)

(52) U.S. Cl. .............................. 378/57; 378/5

(58) Field of Classification Search .............. 378/5, 378/9, 10, 24, 26, 57, 113, 137, 146, 210  
See application file for complete search history.

(56) References Cited

U.S. PATENT DOCUMENTS

| | | | | |
|---|---|---|---|---|
| 3,133,227 A | * | 5/1964 | Brown et al. ............... | 315/5.42 |
| 4,686,695 A | * | 8/1987 | Macovski ................... | 378/146 |
| 4,731,807 A | * | 3/1988 | Plessis et al. ............... | 378/156 |
| 4,768,214 A | * | 8/1988 | Bjorkholm .................. | 378/87 |
| 5,033,073 A | * | 7/1991 | Friddell ...................... | 378/146 |
| 5,218,533 A | * | 6/1993 | Schanen ...................... | 378/9 |
| 5,835,561 A | * | 11/1998 | Moorman et al. ........... | 378/98 |
| 6,433,494 B1 | * | 8/2002 | Kulish et al. ............... | 315/500 |
| 6,507,635 B2 | | 1/2003 | Birdwell et al. | |
| 6,567,496 B1 | * | 5/2003 | Sychev ........................ | 378/57 |
| 7,162,007 B2 | * | 1/2007 | Elyan et al. ................. | 378/57 |
| 7,164,747 B2 | * | 1/2007 | Ellenbogen et al. ......... | 378/19 |
| 2003/0081720 A1 | * | 5/2003 | Swift et al. .................. | 378/41 |
| 2003/0156684 A1 | * | 8/2003 | Fessler ...................... | 378/210 |
| 2003/0231739 A1 | * | 12/2003 | Rosner ........................ | 378/57 |
| 2004/0184574 A1 | * | 9/2004 | Wu et al. ..................... | 378/5 |
| 2004/0264628 A1 | * | 12/2004 | Besson ........................ | 378/5 |
| 2005/0025280 A1 | * | 2/2005 | Schulte ........................ | 378/57 |

* cited by examiner

*Primary Examiner*—Edward J. Glick  
*Assistant Examiner*—Anastasia S. Midkiff  
(74) *Attorney, Agent, or Firm*—Coursey IP Law, P.C.; R. Steven Coursey, Esq.

(57) ABSTRACT

A non-intrusive inspection system, including apparatuses and methods, for non-intrusively inspecting containers such as, without limitation, those employed to transport items in international commerce. The non-intrusive inspection system is configured to generate and scan a container with multiple bremsstrahlung, or x-ray, beams having multiple spectra and directed at the container in multiple directions and planes separated by one or more angle(s). Using data collected from such scanning, software of the non-intrusive inspection system generates three-dimensional images of the items present in a container, calculates the volumes and densities of such items, computes effective "Z" numbers, and distinguishes between multiple materials, or elements, of such items. By employing multiple bremsstrahlung beams directed upon a container in multiple planes, the non-intrusive inspection system reduces the number of orientations and geometries of items within a container that might otherwise be employed to avoid the detection of harmful materials being transported within a container.

35 Claims, 3 Drawing Sheets

ANGLED-BEAM DETECTION SYSTEM FOR CONTAINER INSPECTION

CROSS REFERENCE TO RELATED APPLICATION

This application claims the benefit of priority to U.S. provisional patent application Ser. No. 60/621,261 entitled "Angled-Beam Detection System and Methods for Container Screening and Inspection" and filed on Oct. 22, 2004, now pending.

FIELD OF THE INVENTION

The present invention relates, generally, to the field of non-intrusive inspection systems and, more specifically, to non-intrusive inspection systems and methods for inspecting containers employed, generally, in the cargo transportation industry.

BACKGROUND OF THE INVENTION

Today, only a small percentage of the containers that are employed by the cargo transportation industry to transport goods in international commerce are examined or inspected for contraband when they enter a country on a highway or through a port of entry such as an airport, seaport, or rail port. Such inspection is often conducted by inspectors who physically open the containers and visually (and/or manually) inspect items within the containers. Alternatively, specially trained dogs may sometimes be employed to inspect and, potentially, detect items such as drugs or explosives. Such inspection practices are manpower intensive and take a substantial amount of time per container, thereby making it cost prohibitive to inspect a high percentage of the number of containers that enter a country.

Due to recent terrorist activities and because such a small percentage of the containers are inspected, there is heightened concerned among citizens and government officials alike that terrorists may place nuclear bombs, "dirty" bombs, biological or chemical agents, or other weapons of mass destruction in such containers in order to smuggle them into a country for subsequent use against the citizenry. As a consequence, a number of vendors are developing non-intrusive inspection systems for such containers. Some of the vendors have based their systems on airport baggage scanning systems. Unfortunately, such non-intrusive inspection systems suffer from many difficulties, including that many of the systems do not produce multiple views of the objects present from multiple directions. Also, many of the systems do not provide for the discrimination or identification of materials found in objects present in a container, thereby making the detection of explosives, nuclear materials, and, generally, certain weapons of mass destruction impossible.

Other vendors have developed non-intrusive inspection systems that provide for the discrimination or identification of materials found in containers. However, such systems may be "fooled" by placing items containing different elements in an orientation relative to one another such that the combination of the different elements appears, to such systems, as a different and, possibly, non-harmful element. For example, a first item containing uranium may be positioned with a second item containing cobalt immediately behind the first item. To such material-discriminating non-intrusive inspection systems, the items may appear, together, as a single item containing the non-harmful element, lead. Thus, such material-discriminating non-intrusive inspection systems are not capable of detecting many harmful elements that may be present in containers.

Therefore, there exists in the industry, a need for a non-intrusive inspection system for containers, including apparatuses and methods, that enables the discrimination of materials within such containers independent of their placement and/or orientation relative to one another, and that addresses the above-described, and other, problems, difficulties, and/or shortcomings of current systems.

SUMMARY OF THE INVENTION

Broadly described, the present invention comprises a non-intrusive inspection system, including apparatuses and methods, for non-intrusively inspecting containers employed to transport items or goods therewithin, for generating three-dimensional images of such items within such containers, for calculating the volumes and densities of such items, for distinguishing between multiple materials present in such items, and for detecting harmful, or potentially harmful, materials. More particularly, the present invention comprises a non-intrusive inspection system, including apparatuses and methods, for non-intrusively inspecting containers employed to transport items or goods therewithin that scans each container with multiple bremsstrahlung, or x-ray, beams that define one or more angle(s) therebetween and, correspondingly, define one or more angle(s) with the container. In a further aspect of the present invention, each bremsstrahlung, or x-ray, beam may have multiple spectra corresponding to one or more energy levels.

Advantageously, the non-intrusive inspection system of the present invention enables the inspection and/or screening of containers for the presence of particular items, or objects, therein without requiring inspection personnel to open the containers and perform costly and time-consuming physical or manual inspections thereof. The non-intrusive inspection system of the present invention is, importantly, operable to generate multiple bremsstrahlung, or x-ray, beams for direction at a container in multiple planes that are separated by one or more angle(s). By virtue of the beams being separated by one or more angle(s), the non-intrusive inspection system of the present invention reduces the number of orientations and geometries of items within a container that might otherwise be employed to avoid the detection of harmful, or potentially harmful, materials being brought into a country within a container. The separation of beams by one or more angle(s) also enables the non-intrusive inspection system of the present invention to collect data related to the items present in a container in multiple planes, thereby allowing the non-intrusive inspection system to produce three-dimensional images of such items and to calculate the volumes of such items. In addition, because the bremsstrahlung, or x-ray, beams of the non-intrusive inspection system of the present invention may have pulses of multiple spectra corresponding to multiple energy levels, the non-intrusive inspection system is adapted to distinguish between the materials present in the items of a container and to calculate the effective "Z" numbers (or atomic numbers) and densities of such items.

Further, the non-intrusive inspection system of the present invention provides such capabilities and functionality using a single, multi-energy level, charged particle accelerator that is adapted to generate a pulsed beam of accelerated charged particles having multiple energy levels. By employing only a single, multi-energy level, charged particle accelerator in lieu of multiple charged particle accelerators, the non-intrusive inspection system of the present invention minimizes system, operational, and maintenance costs. It should be understood, however, that the scope of the present invention includes similar non-intrusive inspection systems that may employ multiple charged particle accelerators to produce one or more bremsstrahlung, or x-ray, beams that have one or more spectra for direction at a container at one or more angle(s) therebetween. It should also be understood that the non-intrusive inspection system of the present invention may be utilized to inspect the contents of containers generally used to transport items or goods in international commerce or to inspect the contents of other containers having other sizes and shapes.

Other advantages and benefits of the present invention will become apparent upon reading and understanding the present specification when taken in conjunction with the appended drawings.

DETAILED DESCRIPTION OF THE INVENTION

Figure 1:
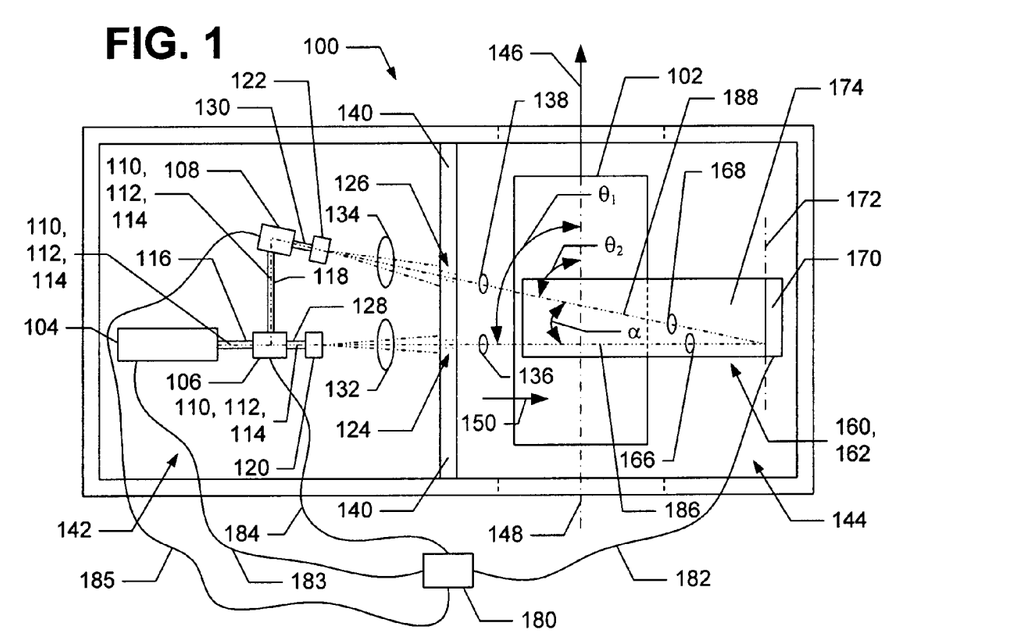
FIG. 1 displays a top plan, schematic view of a non-intrusive inspection system for inspecting the contents of a container in accordance with an exemplary embodiment of the present invention.
Figure 2:
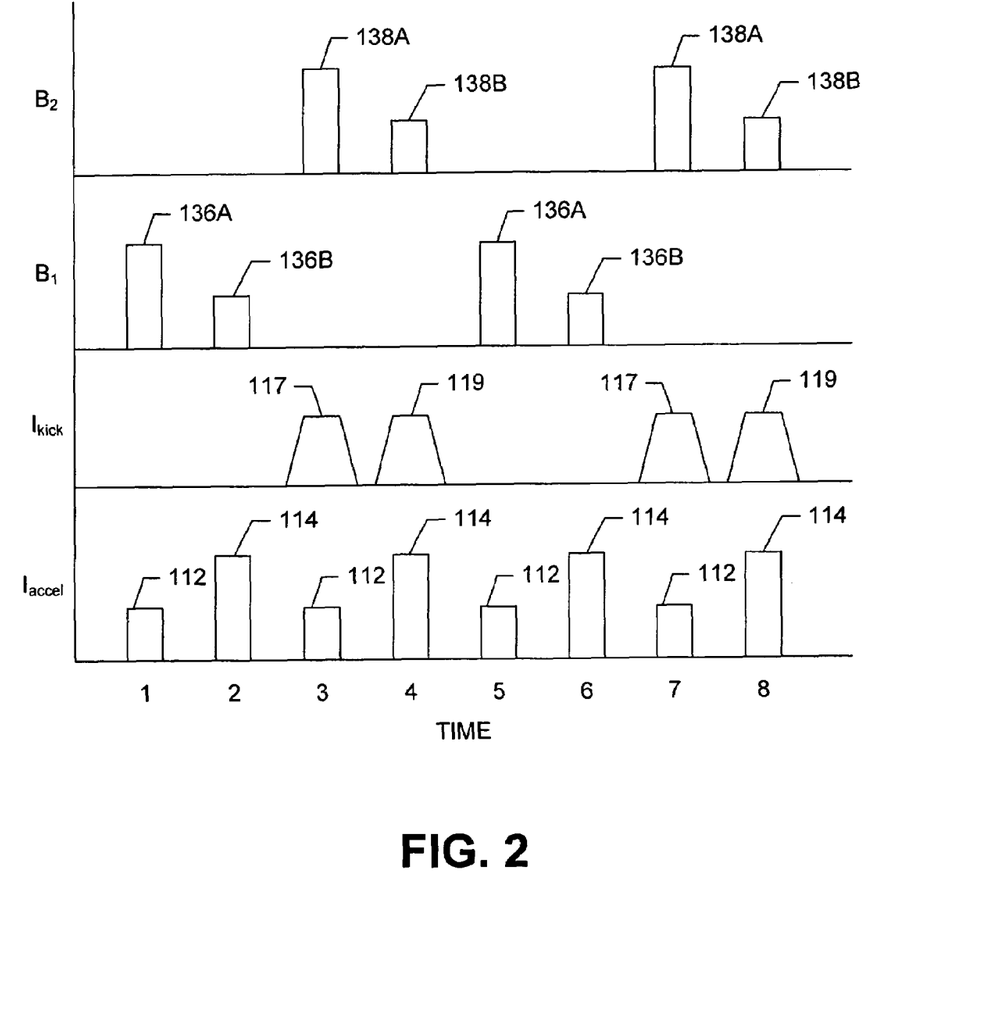
FIG. 2 displays a pictorial timing diagram of a pulsed beam of accelerated electrons having accelerated electrons with multiple energy levels in accordance with the exemplary embodiment of the present invention.

Referring now to the drawings in which like numerals represent like elements or steps throughout the several views, FIG. 1 displays a top plan, schematic view of a non-intrusive inspection system 100, according to an exemplary embodiment of the present invention, for inspecting the contents of a container 102. The non-intrusive inspection system 100 comprises a charged particle accelerator 104 and first and second turning magnets 106, 108 (also, respectively, sometimes referred herein to as "accelerator 104" and "kicker magnets 106, 108"). The charged particle accelerator 104, in the exemplary embodiment, comprises a pulse-type, multi-energy, linear electron accelerator that is operable to produce, or emit, a pulsed beam of accelerated electrons 110 including a first plurality of pulses of accelerated electrons 112 having a first energy level and a second plurality of pulses of accelerated electrons 114 having a second energy level different from the first energy level (see FIG. 2). Generally, the energy levels of the pulses 112, 114 are considered to be in the high energy range for a charged particle accelerator 104, but have appropriate and sufficient spread therebetween such that the bremsstrahlung, or x-ray, spectra resulting therefrom (as described below) may be used for determining effective "Z" numbers for materials present in items within a container 102. The individual pulses 112 of accelerated electrons of the first plurality of pulses 112 and the individual pulses 114 of the second plurality of pulses 114 are emitted such that the pulsed beam of accelerated electrons 110 includes successive pulses of accelerated electrons having energy levels that alternate between the first energy level and the second energy level. Thus, each pulse 112 of accelerated electrons of the first plurality of pulses of accelerated electrons 112 having a first energy level is preceded and followed in the pulsed beam of accelerated electrons 110 by a pulse 114 of the second plurality of pulses of accelerated electrons 114 having a second energy level. Similarly, each pulse 114 of accelerated electrons of the second plurality of pulses of accelerated electrons 114 having a second energy level is preceded and followed in the pulsed beam of accelerated electrons 110 by a pulse 112 of the first plurality of pulses of accelerated electrons 112 having a first energy level.

The first turning magnet 106, as illustrated in FIG. 1, is connected to the output port of accelerator 104 by a vacuum electron beam guide 116 that is adapted to guide, or direct, the pulsed beam of accelerated electrons 110 from the output port of accelerator 104 to the first turning magnet 106 during operation of the non-intrusive inspection system 100. The second turning magnet 108 is connected to the first turning magnet 106 by a vacuum electron beam guide 118 that is configured to guide, or direct, the pulsed beam of accelerated electrons 110, when received during operation as described more fully below, from the first turning magnet 106 toward the second turning magnet 108. The first and second turning magnets 106, 108 are each operable to so guide, or direct, the pulsed beam of accelerated electrons 110 when energized at appropriate times during operation by respective energizing pulses 117, 119 applied thereto. Notably, when no energizing pulse 117, 119 is applied to the first and second turning magnets 106, 108, the direction of travel of the pulsed beam of accelerated electrons 110 is not changed by the first and second turning magnets 106, 108.

The non-intrusive inspection system 100, according to the exemplary embodiment, further comprises first and second conversion targets 120, 122 and respective first and second collimators 124, 126. The first and second conversion targets 120, 122 are connected, respectively, to the first and second turning magnets 106, 108 by vacuum electron beam guides 128, 130. The vacuum electron beam guides 128, 130 are adapted to guide, or direct, the pulsed beam of accelerated electrons 110 from the first and second turning magnets 106, 108, respectively, toward the first and second conversion targets 120, 122. The first and second conversion targets 120, 122 are operable to receive pulses of accelerated electrons 112, 114 of the pulsed beam of accelerated electrons 110 and to convert the received pulses of accelerated electrons 112, 114 into respective pulsed bremsstrahlung, or x-ray, beams 132, 134 that are output from the first and second conversion targets 120, 122 toward respective first and second collimators 124, 126. Generally, the pulsed bremsstrahlung beams 132, 134 include alternating spectra corresponding to the first and second energy levels of the alternating pulses of accelerated electrons 112, 114 of the pulsed beam of accelerated electrons 110 emitted by accelerator 104.

The first and second collimators 124, 126, generally, each include an elongate, narrow opening (e.g., a slot) through which respective portions of the pulsed bremsstrahlung beams 132, 134 pass to create pulsed bremsstrahlung, or x-ray, beams 136, 138 having beam shapes suitable for container inspection. Typically, the pulsed bremsstrahlung, or x-ray, beams 136, 138 each have a fan shape upon exiting respective first and second collimators 124, 126. The first and second collimators 124, 126 are, according to the exemplary embodiment, mounted to and/or integrated into a wall 140 separating an accelerator room 142 in which the accelerator 104, first and second turning magnets 106, 108, and first and second conversion targets 120, 122 reside and an inspection room 144 through which containers 102 are moved and at which the pulsed bremsstrahlung, or x-ray, beams 136, 138 exiting the first and second collimators 124, 126 are directed in order to inspect their contents. During inspection, the containers 102 are, generally, moved in a substantially linear direction of travel (e.g., indicated by arrow 146) along a longitudinal axis 148 of the inspection room 144 that is substantially perpendicular to the predominant direction of travel of the first pulsed bremsstrahlung, or x-ray, beam 136 (e.g., indicated by arrow 150). By moving the containers 102 relative to the pulsed bremsstrahlung, or x-ray, beams 136, 138 and collecting data representative of the portions of beams 136, 138 that pass through the containers 102 and the items therein, the containers 102 and the items therein are scanned.

Figure 3:
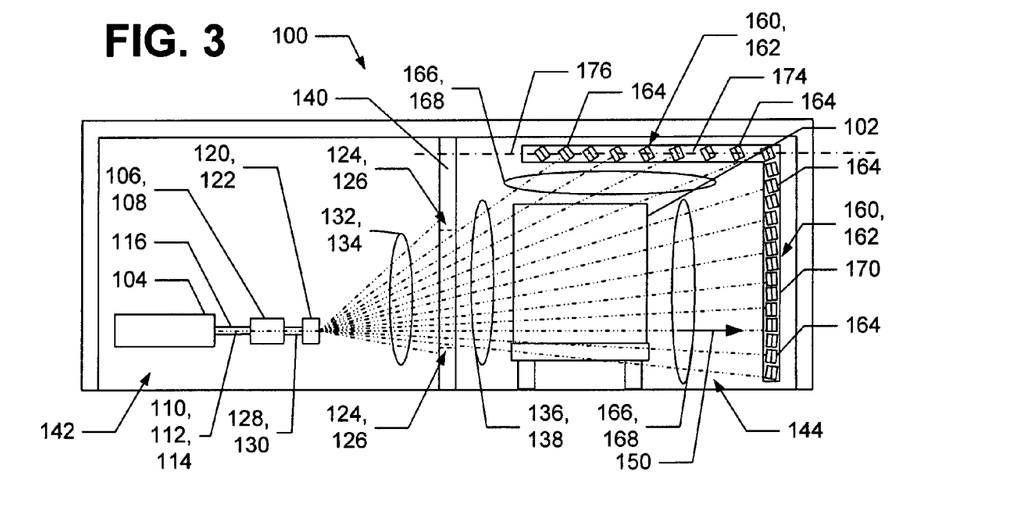
FIG. 3 displays a side, elevational, schematic view of the non-intrusive inspection system of FIG. 1.

The non-intrusive inspection system 100 additionally comprises a detector subsystem 160 having a detector array 162 with a plurality of detectors 164 that are each operable to receive respective portions 166, 168 of the pulsed bremsstrahlung, or x-ray, beams 136, 138 after they pass through a container 102 being inspected within the inspection room 144 and to produce electrical signals, or data, representative of such respective portions 166, 168. As displayed in FIG. 3, the plurality of detectors 164 of the detector array 162 are arranged in a, generally, "L" shape with a first portion 170 of the detector array 162 including detectors 164 oriented in a plane 172 substantially perpendicular to the predominant direction of travel of the first pulsed bremsstrahlung beam 136 (e.g., indicated by arrow 150) and substantially adjacent a side of a container 102 as the container 102 travels through the inspection room 144. A second portion 174 of the detector array 162 includes detectors 164 oriented in a plane 176 substantially perpendicular to the plane 172 of the first portion 170 of the plurality of detectors 164 such that the second portion 174 extends at least partially above a container 102 as the container 102 travels through the inspection room 144. In order to enable the reception of respective portions 166, 168 of the pulsed bremsstrahlung beams 136, 138 that may pass through the top, or roof, of a container 102, some of the individual detectors 164 of the second portion 174 of the detector array 162 are oriented in a direction substantially toward, or facing, the first and second collimators 124, 126 as opposed to being oriented in a direction perpendicular to the top, or roof, of a container 102 passing through the inspection room 144.

The non-intrusive inspection system 100 further comprises a controller 180 that is communicatively connected to the detector subsystem 160 via bidirectional communication link 182, to the charged particle accelerator 104 via a bi-directional communication link 183, to the first turning magnet 106 via bi-directional communication link 184, and to the second turning magnet 108 via bi-directional communication link 185. Generally, the bi-directional communication links 182, 183, 184, 185 comprise one or more appropriate electrical signal cables having one or more electrical signal paths. Bi-directional communication link 182 is adapted to communicate electrical signals (including, but not limited to, control signals and electrical signals, or data, representative of the respective portions 166, 168 of the pulsed bremsstrahlung, or x-ray, beams 136, 138 after they pass through a container 102) between the detector subsystem 160 and the controller 180. Bi-directional communication link 184 is configured to communicate electrical signals (including, without limitation, control, feedback, and other signals) between the controller 180 and the charged particle accelerator 104 that are used by the controller 180 to control the operation of the charged particle accelerator 104 and to insure the generation of pulses having appropriate energy levels at the appropriate times and in the appropriate sequences as described herein. Bi-directional communication links 184, 185 are adapted to communicate electrical signals (including, for example and not limitation, energizing pulses 117, 119, control, feedback, and other signals) between the controller 180 and the first and second turning magnets 106, 108, respectively, that are used by the controller 180 to control the operation of the turning magnets 106, 108 in order to guide, or direct, the pulsed beam of accelerated electrons 110 as described herein.

The controller 180, in accordance with the exemplary embodiment of the present invention, comprises appropriate data communication equipment and one or more computer system(s) configured with appropriate control software and imaging and material discrimination software that are operable when such software is executed thereby, to control the operation of the various components of the non-intrusive inspection system 100, to receive the electrical signals, or data, produced and output by the detectors 164 of the detector array 162, to determine the shapes, volumes, and locations of items present within a scanned container 102, and to produce three-dimensional images of the items present within a scanned container 102 (i.e., using mathematical relationships and software methods generally known to one of reasonable skill in the art) that are displayed to inspection system operators. The controller 180 is also operable, when such software is executed thereby, to receive the electrical signals, or data, produced and output by the detectors 164 of the detector array 162 and to calculate therefrom (i.e., using the mathematical relationships described herein in conjunction with methods generally known to one of reasonable skill in the art) and to display to inspection system operators, the relative and respective densities of the materials, or elements, present within the items of a scanned container 102. Thus, the controller 180 and its imaging and material discrimination software enable inspection system operators to visibly see the locations and shapes of items present within a scanned container 102 (i.e., on a display device of the controller 180) and to be presented with the relative and respective densities of the materials, or elements, of such items. The imaging and material discrimination software may also be configured to cause the controller 180 to generate audible and visible alarms for inspection system operators when a particular material, or element, is detected in an item present in a scanned container 102. For example and not limitation, the imagining and material discrimination software may cause the controller 180 to generate audible and visible alarms if plutonium were detected within in an item present in a scanned container 102.

Figure 4:
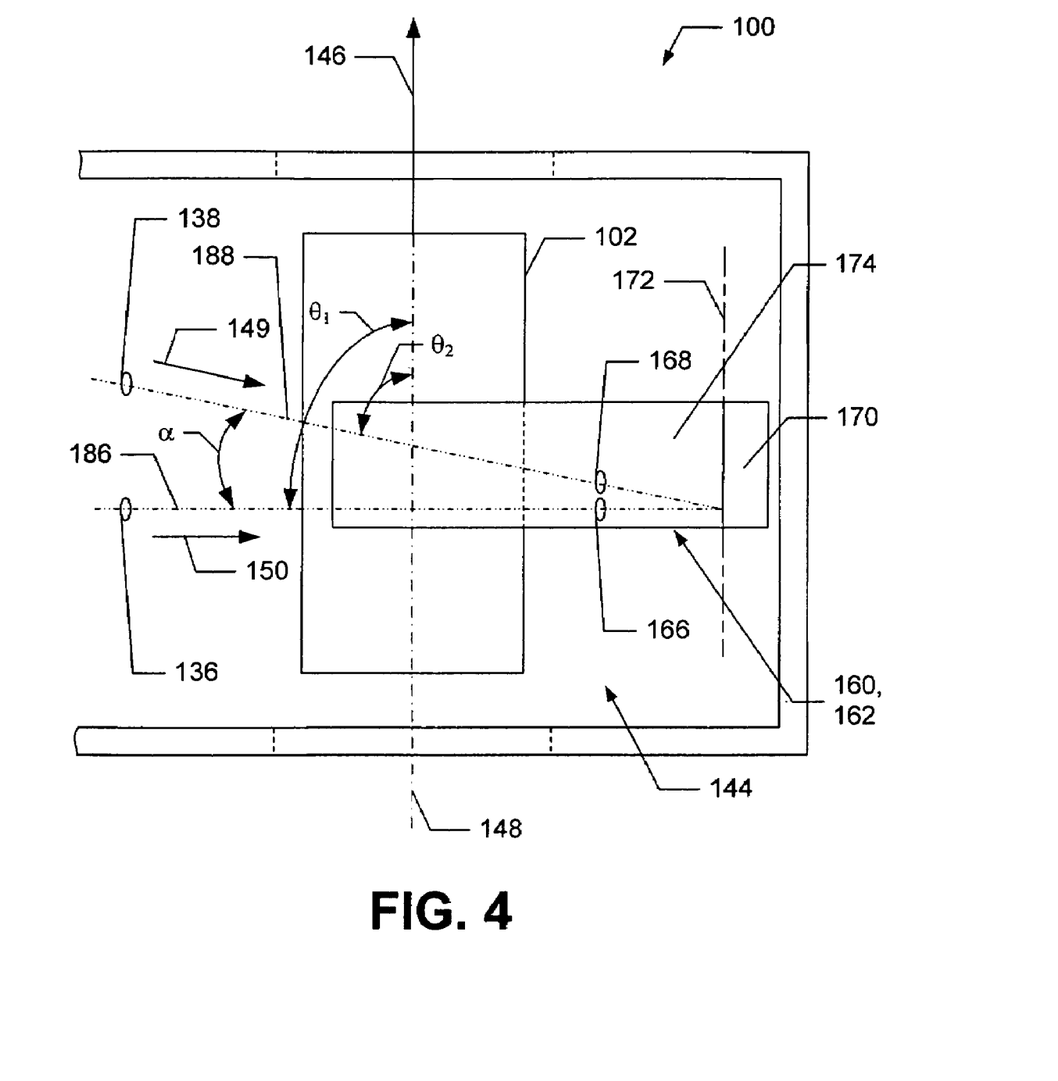
FIG. 4 displays a partial, top plan, schematic view of the non-intrusive inspection system of FIG. 1 more clearly showing an angle between bremsstrahlung, or x-ray, beams alternately impinging on a container being inspected.

Importantly, the accelerator 104, first and second turning magnets 106, 108, first and second conversion targets 120, 122, and first and second collimators 124, 126 are appropriately arranged and oriented so that the first and second pulsed bremsstrahlung, or x-ray, beams 136, 138 exiting the first and second collimators 124, 126 and impinging on a container 102 traveling through the inspection room 144 during scanning and inspection define an angle, a, therebetween (i.e., as illustrated in FIG. 1 and more clearly in the partial, top plan, schematic view of FIG. 4). The first and second pulsed bremsstrahlung, or x-ray, beams 136, 138 lie substantially within respective planes 186, 188 having an angle, $\alpha$, therebetween such that, both beams 136, 138 pass through each point within a container 102 during scanning and inspection of a container 102. The first and second pulsed bremsstrahlung, or x-ray, beams 136, 138 and planes 186, 188 also define respective angles, $\theta_1$ and $\theta_2$, with the direction in which the container 102 travels through the inspection room 144 during inspection. Generally, angle $\theta_1$ has a measure of ninety degrees (90°) and angle $\theta_2$ is the mathematical complement of angle, $\alpha$. Also generally, angle $\theta_2$ and angle $\alpha$ each have measures of less than ninety degrees (90°). By virtue of such arrangement and orientation, the second pulsed bremsstrahlung, or x-ray, beam 138 passes through the container 102 (and every point therein during scanning) in a direction (e.g., indicated by arrow 149) within plane 188 at an angle, $\alpha$, relative to the first pulsed bremsstrahlung, or x-ray, beam 136 within plane 186 and, hence, the portion 168 of the second pulsed bremsstrahlung, or x-ray, beam 138 impinging on detectors 164 of the detector array 162 is substantially at an angle, $\alpha$, relative to the respective portion 166 of the first pulsed bremsstrahlung, or x-ray, beam 136 impinging on detectors 164 of the detector array 162. It should be understood that the scope of the present invention includes angles, $\theta_1$, $\theta_2$, and $\alpha$ having any measures.

By further virtue of such arrangement and orientation and due to the pulsed bremsstrahlung, or x-ray, beams 136, 138 each including consecutive pulses 136A, 136B, 138A, 138B (e.g., the alpha characters designate pulses) having different spectra, the electrical signals generated by the detectors 164 of the detector array 162 at a particular time during inspection of a container 102 are representative of and correspond to the shapes and material densities of the portions of the items within the container 102 lying within planes 186, 188 at such time. Thus, the non-intrusive inspection system 100 of the present invention comprises a "multi-plane" inspection system. Because planes 186, 188 are separated by an angle, $\alpha$, the electrical signals provide stereoscopic data corresponding to the shapes and densities of items within the container 102 and when collected for an entire container 102 (i.e., as the entire container 102 travels through the inspection room 144 and through planes 186, 188) and utilized as inputs by the imaging and material discrimination software of the controller 180, enable the non-intrusive inspection system 100 to produce and display three-dimensional images of the items, or contents, of a scanned container 102 and to calculate the densities of such items or contents. Further, because planes 186, 188 are oriented at angle, $\alpha$, relative to one another and because data is collected at discrete time intervals for each plane 186, 188 as a container 102 travels through the inspection room 144 relative to the planes 186, 188, the non-intrusive inspection system 100 makes it more difficult to pre-arrange the positions of multiple items within the container 102 in order to "hide", render undetectable, or indistinguishable from other items, a particular item within the container 102 containing potentially hazardous or dangerous materials, elements, or substances.

In operation, the accelerator 104 and the first and second turning magnets 106, 108 of the non-intrusive inspection system 100 are appropriately controlled by the controller 180 to produce a pulsed beam of accelerated electrons 110 and alternately direct it at a first conversion target 120 and a second conversion target 122. The pulsed beam of accelerated electrons 110 alternately includes pulses of accelerated electrons 112 having a first energy level and pulses of accelerated electrons 114 having a second energy level. Because the consecutive pulses of accelerated electrons 112, 114 directed at the first and second conversion targets 120, 122 alternate between respective different energy levels, the first and second pulsed bremsstrahlung, or x-ray, beams 132, 134 produced by and exiting from the first and second conversion targets 120, 122 include pulses of alternating first and second spectra corresponding to the first and second energy levels of the alternating pulses of accelerated electrons 112, 114. Further, the first and second pulsed bremsstrahlung, or x-ray, beams 136, 138 produced, respectively, from the first and second bremsstrahlung, or x-ray, beams 132, 134 by first and second collimators 124, 126 similarly include pulses of alternating first and second spectra corresponding to the first and second energy levels of the alternating pulses of accelerated electrons 112, 114.

More specifically, at a first time, the accelerator 104 generates a pulse of accelerated electrons 112 of a first plurality of pulses of accelerated electrons 112 having a first energy level. The pulse of accelerated electrons 112 is directed to the first turning magnet 106 by vacuum electron beam guide 116. Concurrently, no energizing pulse 117 is applied to the first turning magnet 106 by the controller 180, thereby placing the first turning magnet 106 into a de-energized state and allowing the pulse of accelerated electrons 112 to pass through the first turning magnet 106 and on toward the first conversion target 120 via vacuum beam guide 128.

Upon receiving the pulse of accelerated electrons 112 having a first energy level, the first conversion target 120 converts the received pulse of accelerated electrons 112 into a pulse of bremsstrahlung, or x-ray, having first spectra corresponding to the first energy level of the received pulse of accelerated electrons 112. The first conversion target 120 then emits the produced pulse of bremsstrahlung, or x-ray, having first spectra in a direction toward the first collimator 124. While passing through the first collimator 124, the pulse of bremsstrahlung, or x-ray, is shaped to produce a shaped pulse 136A of bremsstrahlung, or x-ray, having a shape (e.g., a fan shape) suitable for inspection of a container 102.

The shaped pulse 136A of bremsstrahlung, or x-ray, having first spectra exits the first collimator 124 traveling substantially within plane 186 in a direction predominantly perpendicular to the direction of travel of the container 102 and impinges upon the container 102 as it is moved through the inspection room 144 during scanning and inspection. The shaped pulse 136A of bremsstrahlung, x-ray, passes through the walls of the container 102 and items present in the container 102 substantially within plane 186. A portion 166 of the shaped pulse 136A of bremsstrahlung, x-ray, passing through the walls of the container 102 and items present in the container 102 strikes detectors 164 of the detector array 162. The detectors 164 then produce and output electrical signals representative of and corresponding to the portion 166 of the shaped pulse 136A of bremsstrahlung, x-ray, impinging thereon and, hence, to the shapes and material densities of the portions of the items within the container 102 lying within plane 186 at such first time.

At a second time immediately subsequent to the first time, the accelerator 104 generates a pulse of accelerated electrons 114 of a second plurality of pulses of accelerated electrons 114 having a second energy level different than the first energy level. The pulse of accelerated electrons 114 is guided to the first turning magnet 106 by vacuum electron beam guide 116. Again, no energizing pulse 117 is concurrently applied to the first turning magnet 106 by the controller 180, thereby maintaining the first turning magnet 106 in a de-energized state and enabling the pulse of accelerated electrons 114 to pass through the first turning magnet 106 and on toward the second conversion target 122 via vacuum beam guide 128.

Similar to the pulse of accelerated electrons 112, upon receiving the pulse of accelerated electrons 114 having a second level at the second time, the first conversion target 120 converts the received pulse of accelerated electrons 114 into a pulse of bremsstrahlung, or x-ray, having second spectra corresponding to the second energy level of the received pulse of accelerated electrons 114. Then, the first conversion target 122 emits the produced pulse of bremsstrahlung, or x-ray, in a direction toward the first collimator 124. While passing through the first collimator 124, the produced pulse of bremsstrahlung, or x-ray, is shaped to produce a shaped pulse 136B of bremsstrahlung, or x-ray, having a beam shape (e.g., a fan shape) suitable for inspection of a container 102.

The shaped pulse 136B of bremsstrahlung, or x-ray, having second spectra exits the first collimator 124 traveling within plane 186 in a direction predominantly perpendicular to the direction of travel of the container 102 and impinges upon the container 102 as it is moved through the inspection room 144 during scanning and inspection. The shaped pulse 136B of bremsstrahlung, or x-ray, passes through the walls of the container 102 and items present in the container 102 within plane 186. A portion 166 of the shaped pulse 136B of bremsstrahlung, or x-ray, passing through the walls of the container 102 and items present in the container 102 then strikes detectors 164 of the detector array 162. The detectors 164 then produce and output electrical signals representative of and corresponding to the portion 166 of the shaped pulse 136B of bremsstrahlung, or x-ray, impinging thereon and, hence, to the shapes and material densities of the portions of the items within the container 102 lying within plane 186 at such second time.

Continuing, at a third time immediately subsequent to the second time, the accelerator 104 generates a pulse of accelerated electrons 112 of a first plurality of pulses of accelerated electrons 112 having a first energy level. The pulse of accelerated electrons 112 is directed to the first turning magnet 106 by vacuum electron beam guide 116. Concurrently, an energizing pulse 117 is applied to the first turning magnet 106 by the controller 180, thereby placing the first turning magnet 106 into an energized state and causing the first turning magnet 106 to direct the pulse of accelerated electrons 112 toward the second turning magnet 108. The pulse of accelerated electrons 112 is guided to the second turning magnet 108 by vacuum electron beam guide 118. An energizing pulse 119 is concurrently applied to the second turning magnet 108 by the controller 180, thereby placing the second turning magnet 108 into an energized state and causing the second turning magnet 108 to guide the pulse of accelerated electrons 112 received from the first turning magnet 106 toward the second conversion target 122 via vacuum beam guide 130.

After receiving the pulse of accelerated electrons 112 having a first energy level, the second conversion target 122 converts the received pulse of accelerated electrons 112 into a pulse of bremsstrahlung, or x-ray, having first spectra corresponding to the first energy level of the received pulse of accelerated electrons 112. The second conversion target 122 then emits the produced pulse of bremsstrahlung, or x-ray, having first spectra in a direction toward the second collimator 126. While passing through the second collimator 126, the pulse of bremsstrahlung, or x-ray, is shaped to produce a shaped pulse 138A of bremsstrahlung, or x-ray, having a shape (e.g., a fan shape) suitable for inspection of a container 102.

The shaped pulse 138A of bremsstrahlung, or x-ray, having first spectra exits the second collimator 126 traveling substantially within plane 188 in a direction at an angle, α, relative to the predominant direction of travel of the shaped pulses 136A, 136B of bremsstrahlung, or x-ray, produced at the first and second times. The shaped pulse 138A of bremsstrahlung, or x-ray, impinges on the container 102 as it is moved through the inspection room 144 during scanning and inspection. The shaped pulse 138A of bremsstrahlung, or x-ray, passes through the walls of the container 102 and items present in the container 102 substantially within plane 188. A portion 168 of the shaped pulse 138A of bremsstrahlung, or x-ray, passing through the walls of the container 102 and items present in the container 102 strikes detectors 164 of the detector array 162. The detectors 164 then produce and output electrical signals representative of and corresponding to the portion 168 of the shaped pulse 138A of bremsstrahlung, or x-ray, impinging thereon and, hence, to the shapes and material densities of the portions of the items within the container 102 lying within plane 188 at such third time.

Subsequently, at a fourth time immediately following the third time, the accelerator 104 generates a pulse of accelerated electrons 114 of a second plurality of pulses of accelerated electrons 114 having a second energy level. The pulse of accelerated electrons 114 is directed to the first turning magnet 106 by vacuum electron beam guide 116. Concurrently, an energizing pulse 117 is applied to the first turning magnet 106 by the controller 180, thereby placing the first turning magnet 106 into an energized state and causing the first turning magnet 106 to direct the pulse of accelerated electrons 114 toward the second turning magnet 108. The pulse of accelerated electrons 114 is guided to the second turning magnet 108 by vacuum electron beam guide 118. An energizing pulse 119 is concurrently applied to the second turning magnet 108 by the controller 180, thereby placing the second turning magnet 108 into an energized state and causing the second turning magnet 108 to guide the pulse of accelerated electrons 114 received from the first turning magnet 106 toward the second conversion target 122 via vacuum beam guide 130.

After receiving the pulse of accelerated electrons 114 having a second energy level, the second conversion target 122 converts the received pulse of accelerated electrons 114 into a pulse of bremsstrahlung, or x-ray, having second spectra corresponding to the second energy level of the received pulse of accelerated electrons 114. The second conversion target 122 then emits the produced pulse of bremsstrahlung, or x-ray, having second spectra in a direction toward the second collimator 126. While passing through the second collimator 126, the pulse of bremsstrahlung, or x-ray, is shaped to produce a shaped pulse 138B of bremsstrahlung, or x-ray, having a shape (e.g., a fan shape) suitable for inspection of a container 102.

The shaped pulse 138B of bremsstrahlung, or x-ray, having second spectra exits the second collimator 126 traveling substantially within plane 188 in a direction at an angle, α, relative to the predominant direction of travel of the shaped pulses 136A, 136B of bremsstrahlung, or x-ray, produced at the first and second times. The shaped pulse 138B of bremsstrahlung, or x-ray, impinges on the container 102 as it is moved through the inspection room 144 during scanning and inspection. The shaped pulse 138B of bremsstrahlung, or x-ray, passes through the walls of the container 102 and items present in the container 102 substantially within plane 188. A portion 168 of the shaped pulse 138B of bremsstrahlung, or x-ray, passing through the walls of the container 102 and items present in the container 102 strikes detectors 164 of the detector array 162. The detectors 164 then produce and output electrical signals representative of and corresponding to the portion 168 of the shaped pulse 138B of bremsstrahlung, or x-ray, impinging thereon and, hence, to the shapes and material densities of the portions of the items within the container 102 lying within plane 188 at such fourth time.

Repetition of the above-described detailed operation of the non-intrusive inspection system 100 at the first, second, third, and fourth times at operational system speeds during the time period necessary for the scanning and inspection of a container 102 moving through the inspection room 144 results in: the accelerator 104 producing and emitting the pulsed beam of accelerated electrons 110 repeatedly including successive pairs of pulses, with each pair of pulses having a pulse of accelerated electrons 112 with a first energy level and a pulse of accelerated electrons 114 with a second energy level; the turning magnets 106, 108 repeatedly and alternately directing the pulsed beam of accelerated electrons 110 first at the first conversion target 120 and then at the second conversion target 122 such that successive pairs of pulses of the pulsed beam of accelerated electrons 110 are alternately directed at the first and second conversion targets 120, 122; and, the first and second conversion targets 120, 122 (i) repeatedly and alternately receiving pairs of pulses of the pulsed beam of accelerated electrons 110, (ii) repeatedly and alternately converting the respectively received pairs of pulses into respective pairs of pulses of bremsstrahlung, or x-ray, of the first or second pulsed bremsstrahlung, or x-ray, beams 132, 134 as the case may be, with each pair of pulses of bremsstrahlung, or x-ray, including a pulse of bremsstrahlung, or x-ray, having first spectra corresponding to the first energy level of a received pulse of accelerated electrons 112 and a pulse of bremsstrahlung, or x-ray, having second spectra corresponding to the second energy level of a received pulse of accelerated electrons 114, and, (iii) repeatedly and alternately emitting the first and second pulsed bremsstrahlung, or x-ray, beams 132, 134 toward the first and second collimators 124, 126 such that the first pulsed bremsstrahlung, or x-ray, beam 132 is directed toward the first collimator 124 and the second pulsed bremsstrahlung, or x-ray, beam 134 is directed toward the second collimator 126.

Such repetition of the above-described detailed operation of the non-intrusive inspection system 100 further results in: the first and second collimators 124, 126 (i) repeatedly and alternately receiving pairs of pulses of the first or second pulsed bremsstrahlung, or x-ray, beams 132, 134, as the case may be, from the first or second conversion targets 120, 122, (ii) repeatedly and alternately shaping the respectively received pairs of pulses of bremsstrahlung, or x-ray, of the first and second pulsed bremsstrahlung; or x-ray, beams 132, 134 into respective shaped pairs of pulses 136A, 136B, 138A, 138B of bremsstrahlung, or x-ray, of respective pulsed bremsstrahlung, or x-ray, beams 136, 138 such that the shaped pairs of pulses 136A, 136B, 138A, 138B are suitable for scanning and inspecting the container 102 then moving through the inspection room 144, (iii) repeatedly and alternately directing the shaped pairs of pulses 136A, 136B, 138A, 138B of pulsed bremsstrahlung, or x-ray, beams 136, 138 toward the container 102 such that the first collimator 124 directs shaped pairs of pulses 136A, 136B of pulsed bremsstrahlung, or x-ray, beam 136 at the container 102 substantially within plane 186 and the second collimator 126 directs shaped pairs of pulses 138A, 138B of pulsed bremsstrahlung, or x-ray, beam 138 at the container 102 substantially within plane 188 and at an angle, α, relative to plane 186; the respective shaped pairs of pulses 136A, 136B, 138A, 138B of pulsed bremsstrahlung, or x-ray, beams 136, 138 alternately passing through the portions of the items of the container 102 that lie within planes 186, 188, as the case may be; and, the detectors 164 of detector array 162 repeatedly and alternately (i) receiving respective portions 166, 168 of pulsed bremsstrahlung, or x-ray, beams 136, 138 that exit the container 102 respectively and substantially in planes 186, 188, and (ii) generating and outputting electrical signals to the controller 180 via communication link 182 such that the electrical signals are respectively representative of the received portions 166, 168 of pulsed bremsstrahlung, or x-ray, beams 136, 138 and, hence, of the shapes and material densities of the portions of the items of the container 102 that lie within planes 186, 188.

Upon repeatedly and alternately receiving electrical signals respectively representative of the received portions 166, 168 of pulsed bremsstrahlung, or x-ray, beams 136, 138 and of the shapes and material densities of the portions of the items of the container 102 that lie within planes 186, 188, the controller 180 converts the corresponding electrical signals received from the detectors 164 into appropriate data and stores the data until it has collected such data for the entire container 102 being scanned and inspected by the non-intrusive inspection system 100. Thus, once all of the data has been collected, the controller 180 has, for its use, an entire container's worth of data for multiple planes 186, 188 of bremsstrahlung, or x-rays, repeatedly slicing through the container 102 (and each point therein) at an angle, α, relative to one another along the container's length at pre-determined time intervals while the container 102 moved through the inspection room 144. The data collected for each plane 186, 188 includes data corresponding to the first and second energy levels of the successive pulses of the pulsed beam of accelerated electrons 110 and, hence, to the first and second spectra of the pulsed bremsstrahlung, or x-ray, beams 136, 138.

Using such collected data and executing its the imaging and material discrimination software, the controller 180 generates three-dimensional images of the contents, or items, present inside the container 102. The controller 180, using the imaging and material discrimination software, next calculates the position and volume of each item present within the container 102. Because the collected data for each plane 186, 188 includes data corresponding to multiple energy levels of accelerated electrons, the controller 180 then computes effective "Z" numbers for each item present inside the container 102.

In order to compute the effective "Z" numbers (or effective atomic numbers) for each item present inside the container 102, the imaging and material discrimination software utilizes and implements equations, physics and mathematical analysis, and mathematical relationships associated with multi-energy material recognition. Generally, the determination of an effective "Z" number for an item is based upon the physical and mathematical relationships corresponding to the loss of intensity of a bremsstrahlung, x-ray, beam as it travels through the various materials or elements thereof. For each material or element traveled through, the bremsstrahlung, or x-ray, beam looses intensity with such loss of intensity being a function of (1) the effective "Z" number (e.g., effective atomic number or composition) of the material, (2) the energy of the beam, and (3) the thickness of the material. Thus, if a bremsstrahlung, or x-ray, beam having pulses of multiple energies (or, for that matter, multiple bremsstrahlung, or x-ray, beams each having pulses of a single energy different than that of the pulses of the other beams) is directed through a number of materials and the beam's loss of intensity is measured or determined at each energy, it is possible to solve certain mathematical relationships, or equations, in order to determine the effective "Z" numbers and thicknesses of each material encountered by the beam.

If, for the sake of simplicity and descriptive purposes, consideration is given to the determination of the effective "Z" number and thickness of a single material through which a bremsstrahlung, or x-ray, beam travels, the final intensity, I (MeV), of the beam emerging from the material may be computed by:

$$I(I_o, \mu, t) = I_o e^{-\mu t}$$

where $I_o$ (MeV) corresponds to the intensity of the beam prior to entering the material, $\mu$ (cm$^2$/g or cm$^{-1}$) corresponds to the material's coefficient of attenuation (described in more detail below), and t corresponds to the material's thickness. Since the material's coefficient of attenuation is dependent upon the material's effective "Z" number, Z, and the energy, $E_{ac}$ (Joules), of the bremsstrahlung, or x-ray, the final intensity of the beam emerging from the material may be computed by:

$$I(I_o, Z, E_{ac}, t) = I_o e^{-\mu(Z, Eac)t}$$

Based on this relationship, a system of two equations and two unknowns may be obtained from two final intensities, two initial intensities, and the two energies that produced them. The system of two equations may then be solved to determine the material's thickness and effective "Z" number.

Before proceeding further, it should be noted that the loss of intensity of a bremsstrahlung, or x-ray, beam traveling through a material results from, among other things, collisions of the beam with the material's atoms. The loss of intensity due to such collisions is mathematically related to the material's coefficient of attenuation, $\mu$. Physically, the material's coefficient of attenuation, $\mu$, is a function of photon cross section, $\sigma$, which is the sum of four properties of the material: (1) photoelectric cross section, $\sigma_\tau$, (2) coherent scattering cross section, $\sigma_{coh}$, (3) incoherent (Compton) scattering, $\sigma_c$, and (4) pair production cross section, $\sigma_\kappa$.

The photon cross section of a particle is an expression of the probability that an incident particle will strike it. As such, photon cross section is strongly related to the total area of a material and the "radius" of the particles within the material. Typically, the photon cross section, $\sigma$, represents the cross-sectional area of a single atom, and consequently, the photon cross section is expressed in units of cm$^2$/atom. Frequently, however, the photon cross section is expressed in units of "barns" instead of cm$^2$, with one barn=$10^{-24}$ cm$^2$.

At the quantum level, the four factors of photon cross section described above, each of which is a function of bremsstrahlung (or x-ray) energy, E, and effective "Z" number, comprise terms or operands when computing the photon cross section. Thus, the photon cross section may be expressed as:

$$\sigma(Z, E) = \sigma_\tau(Z, E) + \sigma_{coh}(Z, E) + \sigma_c(Z, E) + \sigma_\kappa(Z, E).$$

It should be noted that although each term of the above equation may be approximated using the relationships described below, large repositories of known photon cross section data exist for many different materials and may be utilized in lieu of such approximations. Interestingly, in the above equation for photon cross section, the photoelectric cross section, $\sigma_\tau$, term dominates at lower bremsstrahlung, or x-ray, energies (e.g., <0.5 MeV). At higher bremsstrahlung, or x-ray, energies (e.g., >5 MeV), the pair production cross section, $\sigma_\kappa$, term dominates. At intermediate bremsstrahlung, or x-ray, energies (e.g., >0.5 MeV and <5 MeV), the coherent scattering cross section, $\sigma_{coh}$, and incoherent (Compton) scattering, $\sigma_c$, terms dominant the equation. Consequently, material recognition and effective "Z" number determination techniques vary with the energy level of the utilized bremsstrahlung, or x-ray, beam.

The photoelectric effect upon photon cross section, $\sigma$, results from an x-ray/atom collision in which the incident photon's energy is higher than the binding energy of some electron in the atom of the material. In such a collision, the incident photon of the bremsstrahlung, or x-ray, beam is absorbed and in its place, several fluorescent photons and one electron are ejected, thereby ionizing the atom. Naturally, any bremsstrahlung, or x-ray, that is absorbed does not exit the material and impinge upon a detector.

The photoelectric cross section property of a material, $\sigma_\tau$, may be crudely approximated at low energies (e.g., several KeV to hundreds of KeV) by the following expression:

$$\sigma_\tau(Z, E) \approx 10(Z^5/E^3).$$

The coherent scattering effect upon photon cross section, $\tau$, results from an incident photon of the bremsstrahlung, or x-ray, beam making a glancing blow off of an atom of a material, thereby deflecting the bremsstrahlung, or x-ray, away from a detector. For bremsstrahlung, or x-ray, wavelengths less than the diameter of the scattering atoms, the coherent scattering cross section property of a material, $\sigma_{coh}$, may be approximated as follows:

$$\sigma_{coh}(Z, E) \approx 8\pi r_e^2 Z^2 (\lambda/(4\pi a Z^{1/3}))^2 (4/5 - (\lambda/(8aZ^{1/3})))$$

where $\lambda$ is determined by the relationship $E = hc/\lambda$, h is Planck's constant ($6.626068 \times 10^{-34}$ m$^2$ kg/s), c is the speed of light (299,792,458 m/s), $r_e$ is the classical electron radius ($2.817940285 \times 10^{-15}$ m), and a=0.885.

The incoherent (Compton) scattering effect upon photon cross section, $\sigma$, results from an incident photon of the bremsstrahlung, or x-ray, beam knocking out a loosely bound electron of an atom of a material and undergoing a direction change (and energy loss) in the process. Since the direction of the incident photon is changed, it will not impinge upon a detector. The incoherent (Compton) scattering property of a material, $\sigma_c$, may be approximated by the following relationship for bremsstrahlung, or x-ray, beams having energy levels in the medium range:

$$\sigma_c(Z, E) \mp 0.665 \, Z.$$

Notably, the above approximation of the incoherent (Compton) scattering property, $\sigma_c$, is not substantially effected by the energy of the bremsstrahlung, or x-ray, beam and, thus, the approximation does not include energy as an operand.

The pair production cross section effect upon photon cross section, $\sigma$, at relativistic photon energies ($E > 2m_e c^2$—where $m_e$ represents the mass of an electron (e.g., $9.10938188 \times 10^{31}$ kg)) results from an incident photon of the bremsstrahlung, or x-ray, beam impacting an atom of a material and being "consumed" entirely, thereby producing an electron-positron pair. Thus, for relativistic photon energies, the pair production cross section property of a material, $\sigma_\kappa$, may be approximated proportionally as:

$$\sigma_\kappa (Z, E) \propto Z^2 \ln(E-2m_ec^2).$$

At very high energies, E, the pair production cross section property of a material, $\sigma_\kappa$, is effectively constant.

As briefly described above, the total (linear) coefficient of attenuation, $\mu_{tot}$, for a particular material is physically a function of photon cross section, $\sigma$, which is calculated as the sum of the (1) photoelectric cross section, $\sigma_\tau$, (2) coherent scattering cross section, $\sigma_{coh}$, (3) incoherent (Compton) scattering, $\sigma_c$, and (4) pair production cross section, $\sigma_\kappa$. Because the photon cross section, $\sigma$, depends on the effective "Z" number and the energy, $E_{ac}$, of the bremsstrahlung or x-ray beam, the total (linear) coefficient of attenuation, $\mu_{tot}$, for a particular material is also a function of the effective "Z" number and the energy, $E_{ac}$, of the bremsstrahlung or x-ray beam and may be calculated using the following equation:

$$\mu_{tot} (E_{ac}, Z) = \sigma (Z, E_{ac}) \times \rho \times N_A/A$$

where $\mu_{tot}$ is measured in $cm^{-1}$, $\rho$ is the volume density ($g/cm^3$) for an atom of the material, $N_A$ is Avogadro's number ($6.02252 \times 10^{23}$ atom/mole), and A is the atomic mass (g/mole) for the material. Alternatively, the total (linear) coefficient of attenuation, $\mu_{tot}$, may be calculated in $cm^2/g$ as follows:

$$\mu_{tot} (E_{ac}, Z) = \sigma (Z, E_{ac}) \times N_A/A.$$

It should be noted that as with photon cross section data, large repositories of pre-computed coefficients of attenuation exist for many materials and energy ranges. Thus, although the total (linear) coefficient of attenuation, $\mu_{tot}$, may be calculated or approximated using the above equations, it may be desirable to use a pre-computed value therefor obtained from such a repository.

With regard to the thickness, t, of a single material through which a bremsstrahlung, or x-ray, beam travels, if the material's length, L, with respect to the direction of travel of the bremsstrahlung, or x-ray, beam is L cm, then t=L. However, if not, the thickness, t, of a single material may be alternatively defined in $g/cm^2$ in terms of the material's length, L (cm), and the material's density, $\rho$ ($g/cm^3$), as follows:

$$t = L \times \rho.$$

As also briefly described above, a determination of the effective "Z" number and thickness of a single material through which a bremsstrahlung, or x-ray, beam travels may be made, as in the exemplary embodiment, using a bremsstrahlung, or x-ray, beam having pulses of multiple energies (or, for that matter, multiple bremsstrahlung, or x-ray, beams each having pulses of a single energy different than that of the pulses of the other beams) that is directed through the material and measuring the beam's loss of intensity at each energy. Viewed slightly differently, if a bremsstrahlung, or x-ray, beam having alternating pulses of multiple energies (e.g., $E_{LO}$ and $E_{HI}$) and correspondingly alternating intensities (e.g., $I_{LOi}$ and $I_{HIi}$) is directed through a single material and at a plurality of detectors, the corresponding final intensities (e.g., $I_{LO}$ and $I_{HI}$) are measurable by the plurality of detectors. Then, the effective "Z" number and thickness, t, of the material are determinable using the following system of equations:

$$I_{LO} = I_{LOi} e^{-\mu_{tot}(E_{LO}Z)t}$$

$$I_{HI} = I_{HIi} e^{-\mu_{tot}(E_{HI}Z)t}.$$

From these equations, the following equation is obtained:

$$ln(I_{LO}/I_{LOi})/ln(I_{HI}/I_{HIi}) = \mu_{tot}(E_{LO}, Z)/\mu_{tot}(E_{HI}, Z).$$

Consequently, the effective "Z" number of the material, Z, is obtained by minimizing the following function, F:

$$F(Z) = (ln(I_{LO}/I_{LOi})/ln(I_{HI}/I_{HIi}) - \mu_{tot}(E_{LO}, Z)/\mu_{tot}(E_{HI}, Z))^2.$$

Using the effective "Z" number of the material, Z, the thickness, t, of the material is then determined by backsolving either of the following equations:

$$t = -ln(I_{LO}/I_{LOi})/\mu_{tot}(E_{LO}, Z)$$

$$t = -ln(I_{HI}/I_{HIi})/\mu_{tot}(E_{HI}, Z)$$

It should be noted that the above-described method of determining the effective "Z" number and thickness, t, of a material applies only to a single material. If, however, two or more materials were placed in the plane of the bremsstrahlung, or x-ray, beam as is typically encountered with a container 102, the materials would be recognized as a material of a single element and of a single thickness. In order to determine the "Z" numbers and thicknesses for each material placed in the plane of the bremsstrahlung, or x-ray, beam, it is necessary to first determine the minimum number of scanning energies required to differentiate m different kinds of material. If m layers of different materials are present in the plane of a bremsstrahlung, or x-ray, beam having pulses at multiple scanning energies and if $Z_i$ and $t_i$ are, respectively, the atomic number and thickness of the ith material, then the final intensities of the pulses striking detectors of a detector subsystem may be computed by:

$$I (I_0, \{Z_i\}, E_{ac}, \{t_i\}) = I_0 \Pi_{1 \leq i \leq m} e^{-\mu(Z, E_{ac})ti}$$

Using this equation, the minimum number of scanning energies required for determining the "Z" numbers and thicknesses for each material placed in the plane of the bremsstrahlung, or x-ray, beam may be determined.

Once the minimum number of scanning energies has been determined, principles and equations of absorption edge-based recognition and of scattering resulting from photon-electron collisions may be used to ascertain the "Z" numbers and thicknesses of the m different kinds of material placed in the plane of the bremsstrahlung, or x-ray, beam. An absorption edge is a discrete upward spike in the coefficient of attenuation when photon energies are near the binding energies of electrons in the shells of an atom of a material. When the photon energy crosses the binding energy threshold, there is a significantly higher chance that it will ionize the atom. Note that because absorption edges are a photoelectric phenomenon, the energy ranges at which this technique is applicable are in the relatively low photoelectric range.

If the final intensities of the pulses of a bremsstrahlung, or x-ray, beam striking or impinging upon detectors are measured over a range of photon energies, a sharp downward spike will exist at each absorption edge in a material. Because each element above 10 Z has a unique set of absorption edges, measuring final intensities at energies just above and just below these edge energies can yield every element in the path of the beam.

It should be also noted that photon scattering results from a photon-electron collision and that the energy and direction of the scattered photon may be ascertained by modeling the scattering energy and distribution. In order to construct such a model, it is assumed that the impinged upon electron is effectively stationary. If $E_\gamma$ is the energy of an incident photon of a pulse of a bremsstrahlung, or x-ray, beam and if energy and momentum are to be conserved, the following constraints before and after the collision must be obeyed:

$$E_\gamma + m_e c^2 = E'_\gamma + \infty(m_e^2 c^4 + p_e^2 c^2)$$

$$0 = p'_\gamma \sin\theta_\gamma + p'_e \sin\theta_e$$

$$E_\gamma/C = p'_\gamma \cos\theta_\gamma + p'_e \cos\theta_e$$

where $E'_\gamma$ is the photon energy after collision, $\theta_\gamma$ is the scattering angle for the photon, $\theta_e$ is the scattering angle for the electron, $p'_\gamma$ is the momentum of the photon after the collision, and $p'_e$ is the momentum of the electron after the collision. Notably, for a photon of energy E, $p=E/c$ and $m_e c^2$ is the relativistic rest mass energy of an electron.

From the above, when a photon of energy $E_\gamma$ collides with an atom of a material, the polar angle of scattering for the photon, $\theta$, obeys the following constraint:

$$\cos(\theta) = 1 + (1/E_\gamma - 1/E'_\gamma) m_e c^2$$

where in this case, $E'_\gamma$ is the new energy of the photon. Reformulated, the final energy $E'_\gamma$ as a function of $E_\gamma$ and $\theta$ is:

$$E'_\gamma (E, \theta) = E_\gamma [m_e c^2/(m_e c^2 + E_\gamma (1-\cos(\theta)))]$$

From this, it is possible to asymptotically bound the energy of a back-scattered photon, even one with "infinite" energy. At its maximal loss of energy, 180 degree ($\pi$ radian) recoil:

$$\lim_{E_\gamma \to \infty} E'_\gamma (E_\gamma, \pi) \approx 0.255 \text{ MeV}$$

And, for its maximum back-scatter energy, which happens at a 90 degree ($\pi/2$ radian) deflection:

$$\lim_{E_\gamma \to \infty} E'_\gamma (E_\gamma, \pi/2) \approx 0.511 \text{ MeV}$$

Consequently, for worst-case calculations, a maximum photon energy of 0.511 MeV can be used.

When the distribution of the scattering is considered, it becomes useful to speak of the ratio of ($E_\gamma/E'_\gamma$) after and before collision:

$$P(E_\gamma, \theta) = 1/(1 + E_\gamma/m_e c^2 (1-\cos(\theta)))$$

The above equation for final energy provides the final photon energy for any given angle of scatter. It does not, however, provide the probability that a photon will scatter in any one direction. In order to determine such probability, use of the Klein-Nishina formula of the differential cross section is necessary:

$$d\sigma/d\Omega = 0.5 \, r_e^2 \, (P(E_\gamma, \theta) - P(E_\gamma, \theta)^2 \sin^2\theta + P(E_\gamma, \theta)^3)$$

where, as previously, $r_e$ is the classical electron radius. To understand the meaning of this formula, it is necessary to decompose cross section.

Suppose the probability that a photon scatters at all is of not interest, but there is interest in the probability that a photon scatters into a particular region. There is some area around the electron that will scatter a colliding photon of a given energy into a particular region. The particular area around the electron is a partial cross section. If the space around an electron is divided into mutually exclusive regions, there is a partial cross section for each region. The sum of such partial cross sections equals the total cross section.

The Klein-Nishina formula provides a way of knowing how the total cross section changes as the size of the region, $\Omega$, measured in steradians, changes. Here, $d\Omega = 2\pi \sin\theta \, d\theta$. Therefore, the Klein-Nishina formula may be interpreted as "the probability that a photon of energy $E_\gamma$ will scatter off an electron and into the region $2\pi \sin\theta \, d\theta$ is $d\sigma/d\Omega$." With this formula, any possible region into which a photon may scatter can be converted to some part of $\Omega$. Then, by integrating, the size of the cross section that will knock photons into that region is determined. Subsequently, the number of photons of a beam of photons that will be knocked into that region may be determined.

Continuing, the ratio of the logarithmic transparencies of a material at two energies, $E_{\gamma 1}$ and $E_{\gamma 2}$, may be expressed as a function of the energies and Z number:

$$\delta (E_{\gamma 1}, E_{\gamma 2}, Z) = \ln(T_1)/\ln(T_2) = \mu_{tot}(E_{\gamma 1}, Z)/\mu_{tot}(E_{\gamma 2}, Z)$$

The transparencies are determined by directing a beam of bremsstrahlung, or x-rays, having pulses of respective energies $E_{\gamma 1}$ and $E_{\gamma 2}$ through a material and toward detectors. If $\delta$, $E_{\gamma 1}$, and $E_{\gamma 2}$ are known, it is possible to solve for the "Z" number of the material. Transparency, T, is the inverse of absorption and is a function of photon energy $E_{ac}$, the material's thickness, t, and the material's "Z" number as follows:

$$T(E_{ac}, t, Z) = \int_0^{Eac} dP/dE_\gamma (E_{ac}, E_\gamma) \, e^{-\mu(E\gamma, Z)t} \, dE_\gamma / \int_0^{Eac} dP/dE_\gamma (E_{ac}, E_\gamma) \, dE_\gamma$$

Thus, transparency is the ratio of radiation intensity before and after the penetration of a barrier.

In the above equation for transparency, $$dP/dE_\gamma (E_{ac}, E_\gamma) = dI/dE_\gamma (E_{ac}, E_\gamma)(1 - e^{-\mu det(E\gamma)tdet}) \mu^{en}_{det}(E_\gamma)/\mu_{det}(E_\gamma)$$

Given two experimental transparency measurements, $T_{exp1}$ and $T_{exp2}$, of a material, the material's thickness and Z number may be determined by minimizing (in $\lambda$-calculus notation):

$$\lambda (t, Z) \sqrt{((T(E_{ac1}, t, Z) - T_{exp1})^2 + (T(E_{ac2}, t, Z) - T_{exp2})^2)}$$

Even though there may be multiple solutions to the above expression, a solution may be obtained by trying each discrete "Z" number and then searching for the minimal material thickness, t. The transformation to absorption, $\alpha$, from a transparency, T, is:

$$\alpha (T) = (1 - \ln(T))$$

While the foregoing analysis and mathematical relationships enable the determination of effective "Z" numbers for each item of a container 102, they are based on the presumption that data representative of the container's items is collected only within a single plane of bremsstrahlung, or x-ray, passing through each point within the container 102 in a direction substantially perpendicular to the direction of movement of the container 102 during scanning and inspection. Thus, the foregoing analysis and mathematical relationships do not take advantage of the capabilities of the non-intrusive inspection system 100 of the present invention, including its ability to collect data representative of the container's items through the use of multiple beams and planes of bremsstrahlung, or x-ray, passing through each point within the container 102 at angles relative to one another. Through the use of the additional data, the non-intrusive inspection system 100 of the present invention provides calculated effective "Z" numbers having improved accuracy.

In order to do so, the non-intrusive inspection system 100 utilizes a model for the effective "Z" number at each point within a container 102 that treats the effective "Z" number as a vector field having left ($Z_L$), center ($Z_C$), and right ($Z_R$) components such that for a given point within the container 102 denoted by the x, y coordinate pair ($x_T$, $y_T$), the vector field is as follows:

$$Z(x_T, y_T)=[Z_L(x_{T-yT}/\tan\theta), Z_C(x_T), Z_R(x_T+y_T/\tan\theta)]$$

where: +x corresponds to the direction of container 102 travel during scanning and inspection; +y corresponds to the direction perpendicular to the direction of container 102 travel and substantially collinear to the predominant direction of travel of the first pulsed bremsstrahlung, or x-ray, beam 136 (e.g., indicated by arrow 150); +z corresponds to the direction perpendicular to the +x and +y directions in accordance with the right-hand rule; θ is the angle between the +x direction and the bremsstrahlung, or x-ray, beams directed at the container 102; T corresponds to the container 102 or "target"; and, Z corresponds to an effective "Z" number function calculated for the values identified in the parenthesis (e.g., $x_T-y_T/\tan\theta$, $x_T$, and $x_T+y_T/\tan\theta$) for the different components using the above-described analysis, mathematical relationships, and data collected by the detectors 164 of the detector array 162 for left, center, and right bremsstrahlung, or x-ray, beams directed at the container 102 during scanning thereof. It should be noted that because the non-intrusive inspection system 100 of the exemplary embodiment utilizes only two bremsstrahlung, or x-ray, beams 136, 138 (e.g., left and center beams) as seen in FIG. 1, there is no third or right bremsstrahlung, or x-ray, beam and, hence, there is no data collected by the detectors 164 for use in computing a right effective "Z" number component of the effective "Z" number vector field. While this somewhat reduces the improvement in accuracy resulting from the use of the effective "Z" number vector field, the reduction may be acceptable. If not, a third (or right) bremsstrahlung, or x-ray, beam may be employed in an alternate exemplary embodiment of the present invention using another pair of turning magnets in order to produce a third bremsstrahlung, or x-ray, beam having multiple spectra and provide such data and to eliminate the reduction in accuracy present in the current exemplary embodiment.

To use the effective "Z" number vector field to discriminate between materials present in the contents of a container 102, it is necessary to determine a scalar value from the vector field generated for each point within the container 102. One approach is to calculate the magnitude of the effective "Z" number vector field, thereby producing a scalar value comprising a metric average. A second approach is to utilize min Z and voxel rendering to produce a minimal bounding volume. Using the second approach, the accuracy of the effective "Z" number is increased with the angle θ and with the inverse of the width of the target.

Using the effective "Z" numbers and the previously calculated volumes for each item, the controller 180 then calculates the density of each item in the container 102 using the imaging and material discrimination software. Subsequently, when desired by inspection system operators, the controller 180 and the imaging and material discrimination software display or present, to the operators, the three-dimensional images of the contents, or items, present inside the container 102 and the calculated volumes, effective "Z" numbers, and densities of such contents or items.

It should be noted that due to planes 186, 188 being oriented an angle, a, relative to one another, the non-intrusive inspection system 100 is capable of generating three-dimensional images of the contents of a container 102 and of detecting items having materials that might, otherwise, go undetected by similar systems if positioned behind other items in order to, perhaps, avoid detection. It should also be noted that due to the pulsed bremsstrahlung, or x-ray, beams 136, 138 each including pulses of bremsstrahlung, or x-ray, having different spectra, the non-intrusive inspection system 100 is further capable of distinguishing between the materials of items present in a container 102 and of calculating effective "Z" numbers and densities for such items.

It should be understood that the scope of the present invention includes all non-intrusive inspection systems for inspecting containers in which, during inspection of a container, a first bremsstrahlung, or x-ray, beam is passed through the container at an angle relative to a second bremsstrahlung, or x-ray, beam that is also passed through the same container. Further, it should be understood that the scope of the present invention includes such first and second bremsstrahlung, or x-ray, beams comprising pulsed bremsstrahlung, or x-ray, beams, pulsed bremsstrahlung, or x-ray, beams having pulses of different spectra, and/or pulsed bremsstrahlung, or x-ray, beams each having consecutive pulses with different spectra. It should be still further understood that the scope of the present invention includes non-intrusive inspection systems for inspecting containers having a single bremsstrahlung, or x-ray, beam with one or more spectra that is directed at a container at different angles relative to the container during inspection thereof. It should be still further understood that the scope of the present invention includes all non-intrusive inspection systems for inspecting containers having one or more charged particle accelerator(s) that is/are each operable to generate one or more charged particle beam(s) having charged particles with one or more energy level(s).

Whereas the present invention has been described in detail above with respect to an exemplary embodiment thereof, it should be understood that variations and modifications may be effected within the spirit and scope of the present invention, as described herein before and as defined in the appended claims.

What is claimed is:

1. A method for non-intrusively inspecting a container used for the transportation of an item therein, the method comprising:

(a) scanning a container and an item therein with a first x-ray beam at a first angle relative to the container, wherein step (a) of scanning includes the steps of producing the first x-ray beam from a single, multi-energy charged particle beam emitted by a single, stationary, multi-energy level particle accelerator through a first conversion target and moving the container through the first x-ray beam and relative to a single, stationary detector array during a single pass of the container by the single, stationary detector array;

(b) scanning the container and the item therein with a second x-ray beam at a second angle relative to the container, wherein the second angle has an angular measure different than the first angle relative to the container, and wherein step (b) of scanning includes the steps of producing the second x-ray beam from the same single, multi-energy charged particle beam emitted by the single, stationary, multi-energy level particle accelerator and turned by a turning magnet to pass through a second conversion target and moving the container through the second x-ray beam and relative to the same single, stationary detector array during the same single pass of the container by the single, stationary detector array;
(c) producing first data representative of a portion of the first x-ray beam that passes through the container and the item therein;
(d) producing second data representative of a portion of the second x-ray beam that passes through the container and the item therein; and
(e) determining a characteristic of the item based at least in part on said first data and said second data.

2. The method of claim 1, wherein the first x-ray beam includes x-rays having first spectra and x-rays having second spectra different from the first spectra.

3. The method of claim 2, wherein the first spectra corresponds to a first energy level and the second spectra corresponds to a second energy level different from the first energy level.

4. The method of claim 2, wherein the second x-ray beam includes x-rays having first spectra and x-rays having second spectra different from the first spectra.

5. The method of claim 4, wherein the first spectra of the x-rays of the second x-ray beam corresponds to a first energy level and the second spectra of the x-rays of the second x-ray beam corresponds to a second energy level different from the first energy level.

6. The method of claim 4, wherein the first spectra of the x-rays of the first x-ray beam is substantially the same as the first spectra of the x-rays of the second x-ray beam.

7. The method of claim 4, wherein the second spectra of the x-rays of the first x-ray beam is substantially the same as the second spectra of the x-rays of the second x-ray beam.

8. The method of claim 1, wherein the second x-ray beam includes x-rays having first spectra and x-rays having second spectra different from the first spectra.

9. The method of claim 8, wherein the first spectra corresponds to a first energy level and the second spectra corresponds to a second energy level different from the first energy level.

10. The method of claim 1, wherein step (a) includes directing the first x-ray beam at a first portion of the container at a first time and at a second portion of the container at a second time, and wherein the first portion of the container is different from the second portion of the container.

11. The method of claim 1, wherein the characteristic of the item includes the material type of the item.

12. The method of claim 1, wherein the characteristic of the item includes an effective "Z" number for the item.

13. The method of claim 1, wherein the characteristic of the item includes the shape of the item.

14. The method of claim 1, wherein the characteristic of the item includes the location of the item relative to the container.

15. The method of claim 1, wherein the characteristic of the item includes the volume of the item.

16. The method of claim 1, wherein the characteristic of the item includes the density of the item.

17. A method for non-intrusively inspecting a container used for the transportation of an item therein, the method comprising the steps of:
(a) directing a first x-ray beam at a container having an item therein, wherein step (a) of directing includes the steps of guiding a charaed particle beam having multi-energy pulses from a single, stationary, multi-energy level particle accelerator at a first conversion target and moving the container through a first plane defined by the first x-ray beam;
(b) collecting first data representative of at least a portion of the x-rays of the first x-ray beam directed at the container and within the first plane using a single, stationary detector array during a single pass of the container by the single, stationary detector array;
(c) directing a second x-ray beam at the container and at an angle relative to the first x-ray beam, wherein step (c) of directing includes the steps of turning the charged particle beam having multi-energy pulses from the single, stationary, multi-energy level particle accelerator toward a second conversion target and moving the container through a second plane defined by the second x-ray beam;
(d) collecting second data representative of at least a portion of the x-rays of the second x-ray beam directed at the container and within the second plane using the same single, stationary detector array during the same single pass of the container by the single, stationary detector array; and
(e) analyzing the first data and the second data to ascertain an attribute of the item present in the container.

18. The method of claim 17, wherein the method further comprises, prior to step (a), a step (f) of producing the first x-ray beam from a charged particle beam having a first plurality of charged particle pulses with a first energy level and a second plurality of charged particle pulses with a second energy level different from the first energy level.

19. The method of claim 17, wherein the method further comprises, prior to step (c), a step (f) of producing the second x-ray beam from a charged particle beam having a first plurality of charged particle pulses with a first energy level and a second plurality of charged particle pulses with a second energy level different from the first energy level.

20. The method of claim 17, wherein the method further comprises, prior to step (a), a step (f) of producing the first x-ray beam from a charged particle beam, and wherein the method further comprises, prior to step (c), a step (g) of producing the second x-ray beam from the same charged particle beam.

21. The method of claim 17, wherein the method further comprises, prior to step (a), a step (f) of producing the first x-ray beam using a charged particle accelerator, and wherein the method further comprises, prior to step (c), a step (g) of producing the second x-ray beam using the same charged particle accelerator.

22. The method of claim 17, wherein the method further comprises, prior to step (a), a step (f) of producing the first x-ray beam from a charged particle beam having a plurality of charged particle pulses with a first energy level, and wherein the method further comprises, prior to step (c), a step (g) of producing the second x-ray beam from a charged particle beam having a plurality of charged particle pulses with a second energy level.

23. The method of claim 17, wherein the steps of moving the container include moving the container in a direction substantially perpendicular to the direction of at least one of the first x-ray beam and the second x-ray beam.

24. The method of claim 17, wherein the container has a wall, and wherein step (a) includes a step (f) of aiming the first x-ray beam in a direction substantially perpendicular to the wall of the container.

25. The method of claim 17, wherein step (e) includes a step of determining the material type of the item present in the container.

26. The method of claim 17, wherein step (e) includes a step of determining an effective "Z" number for the item present in the container.

27. The method of claim 17, wherein step (e) includes a step of determining the shape of the item present in the container.

28. An apparatus for non-intrusively inspecting a container used for the transportation of an item therein, said apparatus comprising:

a first device for causing a first x-ray beam to be directed in a first direction toward a container having an item therein, said first direction defining a first angle relative to said container, said first device including one multi-energy particle accelerator for emitting a charged particle beam having pulses of charged particles with multiple energy levels;

a second device for causing a second x-ray beam to be directed in a second direction toward said container, said second direction defining a second angle relative to said container different from said first angle, said second device is adapted to receive the charged particle beam from said first device and to guide the received charged particle beam in said second direction;

a single detector array for producing first data representative of at least a portion of said x-rays of said first x-ray beam and for producing second data representative of at least a portion of said x-rays of said second x-ray beam during a single pass of the container by said single detector array; and a controller communicatively connected to said single detector array for receiving said first and second data from said single detector array and for determining a characteristic of said item present in said container by manipulating said first and second data.

29. The apparatus of claim 28, wherein said second devices includes a turning magnet.

30. The apparatus of claim 28, wherein said first x-ray beam includes x-ray having first spectra and x-rays having second spectra different from the first spectra.

31. The apparatus of claim 30, wherein said first spectra corresponds to a first energy level and said second spectra corresponds to a second energy level different from said first energy level.

32. The apparatus of claim 28, wherein said first x-ray beam is produced from a charged particle beam having a first plurality of charged particle pulses with a first energy level and a second plurality of charged particle pulses with a second energy level different from said first energy level.

33. The apparatus of claim 28, wherein said characteristic of said item includes an effective "Z" number.

34. The apparatus of claim 28, wherein said characteristic of said item includes the shape thereof.

35. The apparatus of claim 28, wherein said characteristic of said item includes the location of said item relative to said container.

* * * * *